(12) United States Patent
Zhang

(10) Patent No.: US 11,278,513 B2
(45) Date of Patent: Mar. 22, 2022

(54) DIETHYLAMINO COMPOUNDS FOR USE AS LOCAL ANESTHETICS

(71) Applicant: Zhejiang Yuejia Pharmaceuticals Co., Ltd, Deqing County (CN)

(72) Inventor: Jing Zhang, Shanghai (CN)

(73) Assignee: Zhejiang Yuejia Pharmaceuticals Co., Ltd, Deqing County (CN)

( * ) Notice: Subject to any disclaimer, the term of this patent is extended or adjusted under 35 U.S.C. 154(b) by 25 days.

(21) Appl. No.: 16/764,434

(22) PCT Filed: Sep. 29, 2018

(86) PCT No.: PCT/CN2018/108624
§ 371 (c)(1),
(2) Date: May 15, 2020

(87) PCT Pub. No.: WO2019/095879
PCT Pub. Date: May 23, 2019

(65) Prior Publication Data
US 2020/0352896 A1    Nov. 12, 2020

(30) Foreign Application Priority Data

Nov. 17, 2017 (CN) .......................... 201711144807.2

(51) Int. Cl.
*A61K 31/24* (2006.01)
*A61P 23/02* (2006.01)
*A61K 31/618* (2006.01)

(52) U.S. Cl.
CPC ............ *A61K 31/24* (2013.01); *A61K 31/618* (2013.01); *A61P 23/02* (2018.01)

(58) Field of Classification Search
CPC ...... A61K 31/24; A61K 31/60; A61K 31/618; A61K 9/00; A61P 23/02
See application file for complete search history.

(56) References Cited

U.S. PATENT DOCUMENTS 3,365,483 A    1/1968   Jerzmanowska et al.

FOREIGN PATENT DOCUMENTS

CN    101484415 A    7/2009

OTHER PUBLICATIONS

Manukondakeerthi et al. (Asian journal of Research in Pharmaceutical sciences, 4(3): Jul.-Sep. 2014, pp. 140-150) (Year: 2014).*
Sams-Dodd (Drug discovery today, vol. 10, No. 2, 2005, pp. 139-147 ).*
International Search Report and Written Opinion dated Dec. 24, 2018, for corresponding International Application No. PCT/CN2018/108624, filed on Sep. 29, 2018; consisting of 9-pages.
Nielsen, N.M. et al., "Evaluation of Glycolamide Esters and Various Other Esters of Aspirin as True Aspirin Prodrugs", J. Med Chem., vol. 32, No. 3, 1989, pp. 727-734; consisting of 8-pages.
Wolinsky, J. et al., "Search for Anticholinergic Compounds, XX, synthesis of Aminoalkyl O-, M-, and P-Acetoxybenzoates", Acta Poloniae Pharmaceutica, vol. 37, No. 3, 1980, pp. 275-279; consisting of 5-pages.
Japanese Office Action dated May 17, 2021, for corresponding Japanese Application No. 2020-527054; consisting of 8-pages.
Supplementary European Search Report dated Jul. 2, 2021, for corresponding European Application No. 18878121.5; consisting of 6-pages.
Cope et al., "Benzoates, p-Aminobenzoates and Phenylurethans of 2-Alkylaminoethanols", Contribution from the Chemical Laboratories of Bryn Mawr College and Columbia University, vol. 66, Sep. 1944, pp. 1448-1453; consisting of 6-pages.

* cited by examiner

*Primary Examiner* — Savitha M Rao
(74) *Attorney, Agent, or Firm* — Christopher & Weisberg, P.A.

(57) ABSTRACT

Provided is an application of a compound represented by general formula 1 in the preparation of a local anesthetic. The local anesthetic comprises at least a solid portion and a liquid portion that are separated. The solid portion comprises a therapeutically effective amount of the compound represented by general formula 1. The liquid portion is a pharmaceutically acceptable solvent. The solid portion and the liquid portion are mixed when the local anesthetic is used.

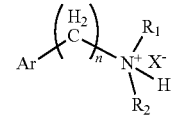

Formula 1

14 Claims, No Drawings

DIETHYLAMINO COMPOUNDS FOR USE AS LOCAL ANESTHETICS

CROSS-REFERENCE TO RELATED APPLICATIONS

This application is a submission under 35 U.S.C. § 371 for U.S. National Stage Patent Application of, and claims priority to, International Application Number PCT/CN2018/108624 entitled LOCAL ANESTHETIC filed Sep. 29, 2019, which is related to and claims priority to Chinese Application Serial No. 201711144807.2, filed Nov. 17, 2017, the entirety of all of which are incorporated herein by reference.

TECHNICAL FIELD

The invention relates to the field of chemical pharmacy, in particular to usage of a compound in preparation of a local anesthetic drug.

BACKGROUND

Chinese Patent CN101484415B discloses an aspirin prodrug (a derivative of acetylsalicylic acid). During treatment, such prodrug can be administered into the body through transdermal administration, achieving the effect of its original drug (aspirin) as a non-steroidal anti-inflammatory drug and avoiding gastrointestinal adverse reactions caused by common oral administration of a non-steroidal anti-inflammatory drug.

However, in practice, the inventor was surprised to find that the prodrugs of such non-steroidal anti-inflammatory drugs can not only be used as "prodrugs", but also produce the effect of local anesthetic drugs, similar to typical local anesthetic drugs of amides, such as lidocaine and bupivacaine.

Local anesthetic drugs are a class of drugs that can locally reversibly block the occurrence and transmission of sensory nerve impulses, referred to as "local anesthetics" for short. According to the type of chemical structure, the local anesthetic drugs can be divided into: p-aminobenzoates (such as procaine and benzocaine), amides (such as lidocaine and bupivacaine), amino ethers and amino ketones (such as dyclonine) etc. It is currently accepted that local anesthetics block voltage-gated Na channels on nerve cell membranes, block conduction, and produce local anesthesia. The effects of local anesthetics are frequency and voltage dependent.

DISCLOSURE OF INVENTION

The present invention provides usage of a compound in preparation of a local anesthetic drug, in particular, usage of a compound represented by Formula (1) in preparation of a local anesthetic drug:

Formula 1

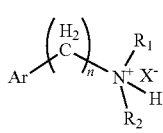

wherein,
Ar— represents

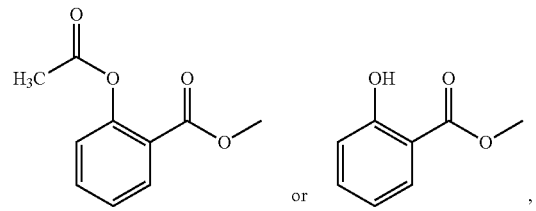

or $R_1$ represents H, C1 alkyl, C2 alkyl, C3 alkyl, C4 alkyl, C5 alkyl or C6 alkyl,
$R_2$ represents H, C1 alkyl, C2 alkyl, C3 alkyl, C4 alkyl, C5 alkyl or C6 alkyl,
$X^-$ represents an anion, n represents 1, 2, 3, 4, 5, 6, 7, 8, 9 or 10.

In a preferred embodiment, $X^-$ represents a monovalent anion, more preferably $Cl^-$, $Br^-$, $F^-$, $I^-$, $AcO^-$, oxalate, dihydrogen phosphate, citrate or thiocyanate group. In another preferred embodiment, $R_1$ represents methyl or ethyl, $R_2$ represents methyl or ethyl. In a further preferred embodiment, n=1 or 2.

In a preferred embodiment, the compound represented by Formula 1 is selected from the group consisting of the following compounds:

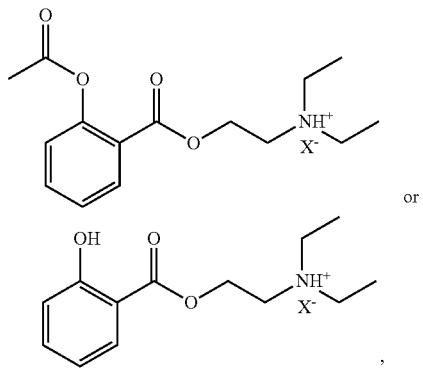

or wherein $X^-$ represents an anion, preferably a monovalent anion, more preferably $Cl^-$, $Br^-$, $F^-$, $I^-$, $AcO^-$, oxalate, dihydrogen phosphate, citrate or thiocyanate group. In a particular embodiment, the compound represented by Formula 1 is 2-(diethylamino)-ethyl-2-acetoxybenzoate hydrochloride, or salicylic acid-(2-diethylaminoethyl ester) hydrochloride.

In a preferred embodiment, the dosage form of the local anesthetic drug is selected from the group consisting of gastrointestinal administration dosage, injection administration dosage, transrespiratory administration dosage, transdermal administration dosage, transmucosal administration dosage, and cavity administration dosage.

In another preferred embodiment, said local anesthetic drug comprises at least a separated solid portion and a separated liquid portion, wherein the solid portion includes a therapeutically effective amount of a compound represented by Formula 1, and the liquid portion includes a pharmaceutically acceptable solvent. Preferably, the pharmaceutically acceptable solvent is selected from the group consisting of sterile water, decarbonated water, ethanol, sorbitol aqueous solution, and physiological saline. More preferably, said solid portion is stored in a hermetic, pharmaceutically acceptable packaging material. The pharmaceutically acceptable packaging material is selected from the group consisting of a low density polyethylene film, a low density polyethylene bag, a high density polyethylene film, a high density polyethylene bottle, a polypropylene bottle, a poly(ethylene terephthalate) bottle, a polyester/aluminum/polyethylene composite film, a polyester/aluminum/polyethylene composite bag, a glass bottle, or a combination thereof.

In a preferred embodiment, when the local anesthetic drug is used, the solid portion is mixed with the liquid portion.

EMBODIMENTS OF INVENTION

In particular, the present invention provides usage of a compound represented by Formula (1) in preparation of a local anesthetic drug:

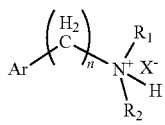

Formula 1 wherein, Ar— represents

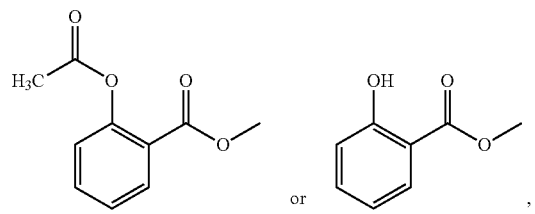

$R_1$ represents H or $C_1$-$C_6$-alkyl, preferably $C_1$-$C_5$-alkyl, more preferably $C_1$-$C_4$-alkyl, even more preferably $C_1$-$C_3$-alkyl, most preferably methyl or ethyl, $R_2$ represents H or $C_1$-$C_6$-alkyl, preferably $C_1$-$C_5$-alkyl, more preferably $C_1$-$C_4$-alkyl, even more preferably $C_1$-$C_3$-alkyl, most preferably methyl or ethyl, $X^-$ represents an anion, preferably a monovalent anion, more preferably $Cl^-$, $Br^-$, $F^-$, $I^-$, $AcO^-$, oxalate, dihydrogen phosphate, citrate and thiocyanate group, n represents 1, 2, 3, 4, 5, 6, 7, 8, 9 or 10; preferably, n is a natural number of less than or equal to 6; more preferably, n is a natural number of less than or equal to 4; most preferably, n is a natural number less than or equal to 3.

The term "$C_1$-$C_6$-alkyl" refers to a straight or branched saturated monovalent hydrocarbon radical having 1, 2, 3, 4, 5 or 6 carbon atoms. Examples of $C_1$-$C_6$-alkyl include methyl, ethyl, propyl, butyl, pentyl, hexyl, isopropyl, isobutyl, sec-butyl, tert-butyl, iso-pentyl, 2-methyl-butyl, 1-methyl-butyl, 1-ethylpropyl, 1,2-dimethylpropyl, neopentyl, 1,1-dimethylpropyl, 4-methylpentyl, 3-methylpentyl, 2-methyl-pentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethyl-butyl, preferably methyl, ethyl, propyl, isopropyl, butyl, sec-butyl or tert-butyl, more preferably methyl or ethyl.

In the present invention, "C1 alkyl" is preferably methyl; "C2 alkyl" is preferably ethyl; "C3 alkyl" is preferably propyl or isopropyl; "C4 alkyl" is preferably butyl, sec-butyl, or tert-butyl.

In a preferred embodiment, the compound represented by Formula 1 is selected from the group consisting of the following compounds:

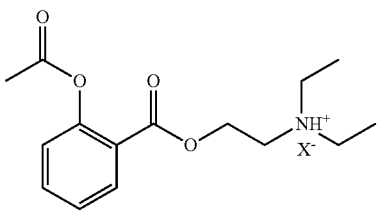

or

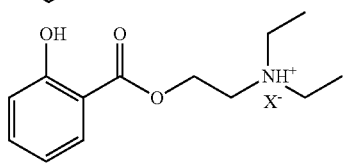

wherein $X^-$ represents an anion, a monovalent anion, more preferably $Cl^-$, $Br^-$, $F^-$, $I^-$, $AcO^-$, oxalate, dihydrogen phosphate, citrate or thiocyanate group. In a particular embodiment, the compound represented by Formula 1 is 2-(diethylamino)-ethyl-2-acetoxybenzoate hydrochloride, or salicylic acid-(2-diethylaminoethyl ester) hydrochloride.

For the preparation method of the compound represented by Formula 1 described in the present invention, reference may be made to Chinese Patent CN101484415 B, U.S. Pat. No. 3,365,483 or other references.

The dosage form of the local anesthetic drug according to the present invention is selected from the group consisting of gastrointestinal administration dosage, injection administration dosage, transrespiratory administration dosage, transdermal administration dosage, transmucosal administration dosage, and cavity administration dosage.

Dosage form for gastrointestinal administration refers to a dosage form in which a pharmaceutical agent enters the gastrointestinal tract after oral administration and plays a local role or a systemic role upon absorption, such as conventional powders, tablets, granules, capsules, solutions, emulsions, suspensions, etc. Dosage form for injection administration includes intravenous injection, intramuscular injection, subcutaneous injection, intradermal injection and intracavity injection. Dosage form for transrespiratory administration includes sprays, aerosols, powders, etc. Dosage form for transdermal administration includes external solutions (sprays, aerosols, powders), lotions, liniments, ointments, plasters, pastes, patches, etc. Dosage form for transmucosal administration includes eye drops, nasal drops, ophthalmic ointments, gargles, sublingual tablets, adhesive tablets, and patches. Dosage form for transcavity administration includes suppositories, aerosols, effervescent tablets, drops and pills, etc., which are used in rectum, vagina, urethra, nasal cavity and ear canal.

The inventor used Chinese Hamster Ovary cells (CHO) stably expressing Nav1.7 and Human Embryonic Kidney cells (HEK) stably expressing Nav1.8 to investigate the inhibition effects of 2-(diethylamino)-ethyl-2-acetoxybenzoate hydrochloride, and salicylic acid-(2-diethylaminoethyl ester) hydrochloride on Nav1.7 and Nav1.8 channel current. For the inhibition of Nav1.7, the $IC_{50}$s of the aforementioned two compounds were 17.67 μM and 24.72 μM, respectively, and for the inhibition of Nav1.8, the $IC_{50}$s of the aforementioned two compounds were 74.64 μM and 73.07 μM, respectively. The $IC_{50}$ reported by a literature for lidocaine on Nav1.7 was 450 μM, and the $IC_{50}$ for Nav1.8 was 104 μM. It is proved that the compound represented by Formula 1 of the present invention has an inhibition effect on Nav1.7 and Nav1.8 channel currents, and the inhibition effect is better than that of lidocaine.

In addition, the inventor used acutely isolated rat dorsal root ganglion (DRG) neurons as the experimental object, using patch clamp technology to investigate the inhibition effect of the compound represented by Formula 1 of the present invention on the neuronal excitability of the dorsal root ganglion. The test results showed that 2-(diethylamino)-ethyl-2-acetoxybenzoate hydrochloride and salicylic acid-(2-diethylaminoethyl ester) hydrochloride can effectively inhibit the action potential of DRG neuron. The $IC_{50}$s thereof were 34.55 μM and 35.02 μM respectively. The $IC_{50}$ of the positive control lidocaine was 37.08 μM. Therefore, it was proved that the compound represented by Formula 1 of the present invention has an inhibition effect on the neuronal electrical activity of DRG cells comparable to that of lidocaine.

However, the inventor has found that the compound represented by Formula 1 cannot exist stably in a solvent for a long time (the solution state is unstable). Therefore, it is necessary to store the solid portion of the drug separately from the solvent. More preferably, the solid portion of the drug can be stored in a hermetic pharmaceutical packaging material, and the stability of the drug can be remarkably improved.

Therefore, in another preferred embodiment, the drug comprises at least a separated solid portion and a separation liquid portion, wherein the solid portion comprises a therapeutically effective amount of the compound represented by Formula 1, and the liquid portion comprises a pharmaceutically acceptable solvent.

As used herein, the term "comprise/include at least . . . " means that the drug can also contain any other components, and these components may be present in any amount, as long as the amounts of the components are acceptable to human body, and for the purposes of the present invention, the activity of the active ingredients in the drug is not adversely affected.

In a preferred embodiment, the solid portion of the drug contains particles formed from the compound represented by Formula 1 with a pharmaceutically acceptable binder.

The term "pharmaceutically acceptable binder" refers to sticky solid powders or thick liquid which can enable aggregation and bonding a non-sticky or less sticky material into granules or compression molding, and is compatible with the active ingredient (i.e., the compound of Formula 1) in the drug of the present invention. That is, it may be blended with a drug without reducing greatly the activity of the drug.

In a preferred embodiment, the binder is selected from the group consisting of hypromellose, carbomer, ethyl cellulose, hydroxypropyl cellulose, vinyl cellulose, starch (more preferably pregelatinized starch), and polyvinyl pyrrolidone. When the solid portion of the pharmaceutical composition contains particles formed from the compound represented by Formula 1 with a pharmaceutically acceptable binder, the particles are mixed with and dissolved in a pharmaceutically acceptable solvent (e.g., sterile water) to form a film after coating and drying. The film is not easy to fall off, and the patient can conveniently attach the drug onto the skin for absorbing.

A common adhesive (e.g., hypromellose, carbomer, ethyl cellulose, hydroxypropyl cellulose, vinyl cellulose, starch or polyvinylpyrrolidone) is mixed with the compound represented by Formula 1 of the present invention, and then the mixture is wet granulated to form particles. The particles are then mixed with and dissolved in a pharmaceutically acceptable solvent (e.g., sterile water). The result shows that the particles formed from hypromellose with the compound represented by Formula 1 have best solubility, and a clear solution is formed. A transparent film is formed after coating and drying, which is not easy to fall off. The patient can conveniently adhere the drug to the skin for absorbing. Thus, in a preferred embodiment, the pharmaceutically acceptable binder is hypromellose.

The "repose angle" formed by stacking the powders or particles reflects its fluidity. The term "repose angle" generally refers to the maximum angle formed by the free slope of the layer of the stacked powders or particles and the horizontal plane. The smaller the repose angle, the smaller the friction between the powders or particles, and the better the fluidity. Better fluidity is more convenient for dissolution and use of the powders or particles. In a preferred embodiment, the repose angle of the powders or particles is less than or equal to 40'; in a more preferred embodiment, the repose angle of the powders or particles is less than or equal to 35°; and in an even more preferred embodiment, the repose angle of the powders or particles is less than or equal to 30°.

In another preferred embodiment, the solid portion of the drug of the present invention is stored in a sealed, pharmaceutically acceptable packaging material.

The term "pharmaceutically acceptable packaging material" refers to such a packaging material that the container/sealing material and the content therein have no severe interaction. That is, the interaction, if any, does not result in a change in product activity and stability, or creates a risk of toxicity. Under normal storage/use condition, any interaction between the package material and the product does not result in unacceptable variations in product quality or packaging. The pharmaceutically acceptable packaging materials include, but are not limited to, low density polyethylene films, low density polyethylene bags, high density polyethylene films, high density polyethylene bottles, polypropylene bottles, poly(ethylene terephthalate) bottles, polyester/aluminum/polyethylene composite films, polyester/aluminum/polyethylene composite bags, or combinations thereof. In a preferred embodiment, the pharmaceutically acceptable packaging material is a combination of a high density polyethylene bottle and a polyester/aluminum/polyethylene composite bag.

In another preferred embodiment, the liquid portion of the drug of the present invention comprises a pharmaceutically acceptable solvent. The pharmaceutically acceptable solvents include, but are not limited to, sterile water, decarbonated water, ethanol, sorbitol aqueous solution, physiological saline, and the like.

In a preferred embodiment, the drug further comprises a pharmaceutical spray device, a medicinal dropper, a medicinal soft brush, or a combination thereof. The solid portion of the drug, when used, mixes with the liquid portion to form a spray, a drop, or an inunction.

In a particular embodiment, the solid portion (particles) of the drug is packaged with a high density polyethylene bottle and then placed in a composite bag of polyester/aluminum/polyethylene for drug packaging. The liquid portion comprises sterile water as a solvent (stored in a pharmaceutical glass bottle or a pharmaceutical polyethylene plastic bottle). The solid portion and the liquid portion are placed in a plastic tray with a pharmaceutical spray device, such as a pharmaceutical spray pump, and then are together placed in a white card carton. It should be noted that in order to facilitate the use by a patient, the particles and the solvent may be packaged in advance in a given ratio, such as 5 g of particles and 50 mL of sterile water. When used by a patient, 5 g of the particles are all dissolved in 50 mL of sterile water to form a 10% aqueous solution which is then used with a pharmaceutical spray pump to form a spray (the aqueous solution is for use within a specified period of time, for example, 1-2 weeks).

It should be noted that any combination of the techniques described herein may be implemented.

The invention is further illustrated with specific examples. It should be understood that these examples are merely illustrative of the invention and are not intended to limit the scope of the invention. In the methods of the following examples, if the specific conditions are not specified, conventional conditions or conditions as suggested by the manufacturer may be applicable. All percentages, ratios, proportions, or parts are by weight unless otherwise specified.

Units in a weight/volume percentage in the present invention are well known to those skilled in the art. For example, the weight/volume percentage may refer to the weight (grams) of a solute in 100 milliliters of a solution.

Unless otherwise specified, all technical and scientific terms used herein have the same meaning as commonly understood by one of ordinary skill in the art. In addition, any methods and materials similar or equivalent to those described may be employed in the present invention. The preferred embodiments and materials described herein are exemplary only.

Example 1: Preparation of 2-(diethylamino)-ethyl-2-acetoxybenzoate hydrochloride Using toluene as the solvent and N, N-dimethylformamide as the catalyst, aspirin and sulfoxide chloride were reacted at an equivalent ratio of 1:1.1 at a reaction temperature of 50° C. for 2 hours to produce o-acetylsalicyloyl chloride. Then, diethylaminoethanol and the acylation product o-acetylsalicyloyl chloride were reacted at an equivalent ratio of 1:1 at a reaction temperature of 25° C. for 4 hours, producing 2-(diethylamino)-ethyl 2-acetoxybenzoate. The aqueous phase was extracted with methyl tert-butyl ether, and the aqueous phase was taken into an ice bath. Sodium bicarbonate was added to adjust the pH to 7-8, and then isopropyl acetate was used as the extractant to extract the aqueous phase. The isopropyl acetate phase was taken. Isopropyl acetate was used as the solvent in the salt formation process, and then the amount of hydrogen chloride gas introduced was strictly controlled, so that the pH of the reaction solution was about 3.5. After the completion of the reaction, 2-(diethylamino)ethyl 2-acetoxybenzoate hydrochloride crude raw material was obtained.

Under heating and reflux, anhydrous acetonitrile was continuously added to the crude raw material of 2-(diethylamino)ethyl 2-acetoxybenzoate hydrochloride with stirring, until 2-(diethylamino)ethyl 2-acetoxybenzoate hydrochloride was completely dissolved. The final mass/volume ratio of the crude raw material of 2-(diethylamino)ethyl 2-acetoxybenzoate hydrochloride to anhydrous acetonitrile is 1:4. After slowly cooling to 25° C., white crystals were precipitated, and the solid was vacuum-dried after suction filtration.

The physical and chemical properties of the synthesized crystals of 2-(diethylamino)-ethyl-2-acetoxybenzoate hydrochloride are shown in Table 1.

TABLE 1

| Physical and Chemical Properties | Description |
|---|---|
| Morphology | White or white-like powders |
| Melting point | 136.0-139.0° C. |
| Repose angle | 42° |
| Solubility | This product is extremely soluble in water; very soluble in chloroform or methanol; soluble in ethanol; slightly soluble in acetone; insoluble in ethyl acetate and ether. |
| Acidity | The pH value of the 2% aqueous solution of this product at 25 ± 0.5° C. is 4.0-6.0 |
| Dissociation constant | 8.82 |

The synthesized 2-(diethylamino)-ethyl-2-acetoxybenzoate hydrochloride crystals were taken for NMR characterization, using Bruker AV-500 Superconducting NMR instrument, at a temperature of 300.0K. The solvent was CDCl3. The the characteristic data obtained are shown below, proving that the structure of the obtained product is consistent with 2-(diethylamino)-ethyl-2-acetoxybenzoate hydrochloride.

$^{13}$C NMR (400 MHz, CDCl3): δ8.49, 20.92, 47.17, 49.74, 58.80, 122.03, 123.73, 126.05, 131.15, 134.45, 150.73, 163.52, 169.45. $^{1}$H NMR (400 MHz, CDCl3): δ1.42 (t, 6H, J=7.5 Hz), 2.35 (s, 3H), 3.23 (m, 4H), 3.42 (m, 2H), 4.85 (t, 2H, J=5.5 Hz), 7.14 (d, 1H, J=8.0 Hz), 7.34 (dd, 1H, J=8.0 Hz), 7.61 (dd, 1H, J=7.5 Hz), 8.00 (d, 1H, J=8.0 Hz), 12.54 (s, 1H).

Example 2: Stability of Aqueous Solution of 2-(diethylamino)-ethyl-2-acetoxybenzoate hydrochloride 5 g of 2-(diethylamino)-ethyl-2-acetoxybenzoate hydrochloride prepared in Example 1 was dissolved in 50 mL of sterile water and placed at 2-8° C. Samples were taken on day 0, month 0.5, month 1, month 2 and month 3 to detect the contents of the main drug and specific impurities (salicylic acid-(2-diethylaminoethyl ester) hydrochloride, acetylsalicylic acid, salicylic acid) and related substances, wherein the content of the main drug and specific impurities were detected by high-performance liquid chromatography (external standard method), and the related substances were detected by high-performance liquid chromatography (principal component self-control method without correction factors). The conditions of HPLC were as follows:

Column: Inertsil ODS-3 (250×4.6 mm, 5 μm) or equivalent

Flow rate: 1.0 ml/min

Column temperature: 33° C.

Wavelength: 276 nm, 303 nm

Injection volume: 10 μl

Mobile phase: water (15 ml of triethylamine+3.5 ml of 10% tetrabutylammonium hydroxide, adding water to 1000 ml):methanol:glacial acetic acid (63:27:10).

The results of the stability study showed that after the aqueous solution of 2-(diethylamino)-ethyl-2-acetoxybenzoate hydrochloride was placed at 2-8° C. for 3 months, the content of the main drug was reduced to 86%, and the content of the impurity salicylic acid-(2-diethylaminoethyl ester) hydrochloride rose to more than 13%. Such results did not meet the general requirements for chemical drug stability. The specific data are shown in Table 2.

TABLE 2

| Items | Time (Month) | | | | |
|---|---|---|---|---|---|
| | 0 | 0.5 | 1 | 2 | 3 |
| Main Drug, % | 99.48 | 99.32 | 97.59 | 94.86 | 86.55 |
| Salicylic acid-(2-diethylaminoethyl ester) hydrochloride, % | 0.51 | 0.67 | 2.38 | 5.09 | 13.35 |
| Acetylsalicylic acid, % | Not detected | Not detected | 0.018 | 0.033 | 0.042 |
| Salicylic acid, % | 0.0028 | 0.0035 | 0.0044 | 0.012 | 0.049 |
| Related substances, % | Not detected | Not detected | Not detected | Not detected | Not detected |

Example 3: Preparation of 2-(diethylamino)-ethyl-2-acetoxybenzoate hydrochloride Particles (1) 2-(diethylamino)-ethyl-2-acetoxybenzoate hydrochloride obtained in Example 1 was screened with an 80-mesh screen.

(2) Formulation of 1.5% hypromellose solution: 1.5 g hypromellose was dissolved in 100 g hot water, with stirring to homogeneity, and the solution stood overnight at room temperature for standby.

(3) 100 g of 2-(diethylamino)-ethyl-2-acetoxybenzoate hydrochloride pretreated in step (1) was mixed with 1.5 g of hypromellose dry powders, and 9-10 g of hypromellose solution prepared in step (2) was added to mix uniformly, producing a soft material. The soft material was pressed through a 14-mesh screen.

(4) The soft material was dried at 60° C. for 4-6 hours.

(5) The dried soft material was granulated and the particles that could pass through a 10-mesh screen but couldn't pass through a 60-mesh screen were selected.

The resultant particles of 2-(diethylamino)-ethyl-2-acetoxybenzoate hydrochloride were white-like, and had a repose angle of 28°. The pH value of the aqueous solution at 25±0.5° C. was 4.3-4.4.

Example 4: Stability Study of Particles of 2-(diethylamino)-ethyl-2-acetoxybenzoate hydrochloride 5 g of the particles of 2-(diethylamino)-ethyl-2-acetoxybenzoate hydrochloride prepared in Example 3 were packaged in a high density polyethylene bottle and sealed, and the bottle was placed in a packaging composite bag of polyester/aluminum/polyethylene for drug. Sterile water (50 mL) was used as a solvent (stored in a medicinal glass bottle or a medicinal polyethylene plastic bottle), and was placed in a plastic tray with the packaged particles. Then, they were together placed in a white card carton. Before use, a patient could mix them to formulate, for example, eye drops for use.

The above prepared particles of 2-(diethylamino)-ethyl-2-acetoxybenzoate hydrochloride (packaged in a high density polyethylene bottle, sealed and placed in a packaging composite bag of polyester/aluminum/polyethylene for drug) were stored at 25° C.±2° C. and 60%±10% relative humidity for 0 month, 3 months, 6 months, 9 months, 12 months. Morphology, dry weight loss, moisture, specific impurities (salicylic acid-(2-diethylaminoethyl ester) hydrochloride, acetylsalicylic acid, salicylic acid), related substances, and the content of the main drug were detected. The morphology was determined visually. The moisture was detected by a volumetric titration method (the volumetric titration method of the Fischer-Tropsch method in "Chinese Pharmacopoeia"). The contents of the specific impurities and the main drug were detected by high-performance liquid chromatography (external standard method), and the related substances were detected by adopting high-performance liquid chromatography (principal component self-control method without correction factors). The conditions of the high performance liquid chromatography were the same as those in Example 2.

The results of the stability study showed that, after the particles were placed at 25° C.±2° C. for 12 months, the stability was very good, and various physicochemical parameters were substantially unchanged. The data are shown in Table 3.

TABLE 3

| Items | Time (Month) | | | | |
|---|---|---|---|---|---|
| | 0 | 3 | 6 | 9 | 12 |
| Morphology | White-like particles | White-like particles | White-like particles | White-like particles | White-like particles |
| Dry weight loss, % | 0.53 | 0.43 | 0.44 | 0.44 | 0.49 |
| Moisture, % | 0.33 | 0.14 | 0.19 | 0.16 | 0.21 |
| Salicylic acid-(2-diethylaminoethyl ester) hydrochloride, % | 0.34 | 0.33 | 0.34 | 0.34 | 0.38 |
| Acetylsalicylic acid, % | Not detected | Not detected | Not detected | Not detected | Not detected |
| Salicylic acid, % | 0.0013 | 0.0022 | 0.0025 | 0.0036 | 0.0031 |
| Related substances, % | 0.031 | 0.025 | 0.022 | 0.021 | 0.027 |
| Main drug, % | 99.7 | 99.4 | 99.5 | 99.7 | 99.6 |

Example 5: Synthesis of salicylic acid-(2-diethylaminoethyl ester) hydrochloride 2-(diethylamino)-ethyl-2-acetoxybenzoate hydrochloride (31.5 g) obtained in Example 1 was dissolved in acetonitrile (30 mL), and concentrated hydrochloric acid (10 mL) was added, with stirring at room temperature for 48 hours. The solution was concentrated and evaporated to dry, and 50 mL of water was added to dissolve the dried substance. Saturated sodium bicarbonate solution was added with stirring. The solution was extracted with isopropyl acetate, washed with saturated brine, and dried over anhydrous sodium sulfate. It was filtered, and HCl gas was introduced. White solid was precipitated. The solid was recrystallized from ethanol to obtain salicylic acid-(2-diethylaminoethyl ester) hydrochloride (17.7 g, yield: 65%).

HNMR (CDCl$_3$) δ (ppm): 11.31 (br, 1H), 10.47 (s, 1H), 7.87 (dd, J=8.0, 1.5 Hz, 1H), 7.52-7.49 (m, 1H), 7.03 (d, J=8.0 Hz, 1H), 6.95-6.92 (m, 1H), 4.69 (t, J=5.0 Hz, 2H), 3.52 (q, J=4.5 Hz, 2H), 3.24-3.17 (m, 4H), 1.30-1.25 (m, 6H).

Example 6: The Anesthetic Effect of the Compound on the Corneal Surface of New Zealand Rabbits New Zealand white rabbits were weighed. According to the weight, the rabbits were randomly divided into 5 groups: the group of 2-(diethylamino)-ethyl-2-acetoxybenzoate hydrochloride, the group of salicylic acid-(2-diethylaminoethyl ester) hydrochloride, the group of aspirin, the group of sodium salicylate, and the positive control lidocaine group. A single administration of 3 mg/animal (100 µL) was performed on the surface of the eyeball, and the drug concentration was 3% (m/V) in each case (wherein a Tris solution was added to aspirin to facilitate dissolution). Each group included 12 rabbits.

Before administration, 1 g of Von Frey fiber filament was used to induce corneal reflex in rabbits, and the number of rabbit blinks caused by 10 stimulations was recorded. Then, 100 μL of the test liquid samples were dropped correspondingly onto the left eyeballs of the rabbits of each group: 3% 2-(diethylamino)-ethyl-2-acetoxybenzoate hydrochloride, 3% salicylate acid-(2-diethylaminoethyl ester) hydrochloride, 3% aspirin, 3% sodium salicylate, 3% lidocaine. An equal volume of normal saline was dropped onto the right eyeball as the self-negative control. Within 30 minutes after administration, the test was conducted every 5 minutes, and the number of rabbit blinks caused by 10 stimulations at each time point was recorded. After 30 minutes of administration, it was tested every 15 minutes. After the corneal reflex returned to the pre-dose level, the test was stopped.

By comparing the corneal reflex on the administration side and the self-negative control side, the effect of the compound on the corneal reflex after administration was judged. Corneal reflex inhibition (CRI) was used to evaluate the effect of drugs on corneal reflex. CRI was calculated as follows:

CRI %=(10−number of blinks)/10*100%

The results were shown in Table 4. Results of positive control lidocaine, 2-(diethylamino)-ethyl-2-acetoxybenzoate hydrochloride, and salicylic acid-(2-diethylaminoethyl ester) hydrochloride showed that, at the earliest detection time point (5 min after administration) after the left eyeball was dropped with the corresponding test liquids, the CRI (%) of these three groups of compounds was significantly increased (p<0.001), relative to the self-negative control (CRI (%) was 0.0±0.0) of the right eyeball. The inhibition effect on corneal reflex was still significant at 45 min or 30 min after administration (p<0.001 or p<0.01). It was proved that 2-(diethylamino)-ethyl-2-acetoxybenzoate hydrochloride, and salicylic acid-(2-diethylaminoethyl) hydrochloride had a local anesthesia effect for ophthalmic administration, with quick onset. However, aspirin and sodium salicylate had no local anesthetic effect at all, and their CRI (%) as well as CRI (%) of negative controls were 0.0±0.0.

the present invention is broadly defined in the scope of the claims. If any product or method found by any other part falls into the scope of the claims, it is an equivalent of the present invention, and should be covered by the scope of the claims.

The invention claimed is:

1. A method of use of a compound represented by formula (1) for a local anesthetic, comprising the step of administering the compound represented by formula (1) to a subject in need thereof through gastrointestinal administration, injection administration, transrespiratory administration, transdermal administration, transmucosal administration, and cavity administration:

Formula 1

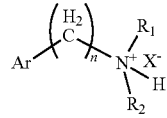

where,
Ar— represents

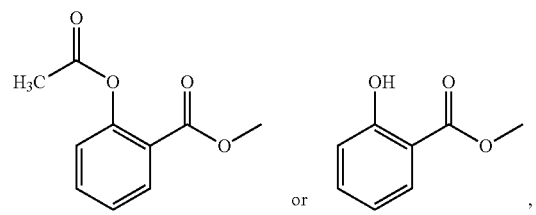

$R_1$ represents H, C1 alkyl, C2 alkyl, C3 alkyl, or C4 alkyl,
$R_2$ represents H, C1 alkyl, C2 alkyl, C3 alkyl, or C4 alkyl,
$X^-$ represents an anion, and
n represents 1, 2, 3, 4, 5, or 6.

2. The method of use of the compound of claim 1, wherein $X^-$ represents a monovalent anion.

TABLE 4

| Test Solutions | CRI (%) at different time after administration | | | | | | | | |
|---|---|---|---|---|---|---|---|---|---|
| | 0 min | 5 min | 10 min | 15 min | 20 min | 25 min | 30 min | 45 min | 60 min |
| Saline (Self-negative control | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 |
| 2-(diethylamino-ethyl-2-acetoxybenzoate hydrochloride | 0.0 ± 0.0 | 99.1 ± 2.0 *** | 97.2 ± 2.9 *** | 96.7 ± 6.5 *** | 86.7 ± 9.8 *** | 77.5 ± 2.9 *** | 57.5 ± 12.2 *** | 12.2 ± 12.4 ** | 0.0 ± 0.0 |
| Salicylate acid-(2-diethylaminoethyl ester) hydrochloride | 0.0 ± 0.0 | 99.2 ± 2.9 *** | 96.7 ± 6.5 *** | 95.9 ± 9.8 *** | 87.5 ± 11.9 *** | 79.4 ± 12.2 *** | 60.2 ± 12.4 ** | 13.5 ± 9.9 ** | 0.0 ± 0.0 |
| Aspirin | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 |
| Sodium salicylate | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 |
| Lidocaine | 0.0 ± 0.0 | 98.3 ± 3.9 *** | 95.0 ± 10.0 *** | 91.7 ± 15.3 *** | 86.7 ± 21.0 *** | 82.5 ± 27.3 *** | 70.0 ± 27.3 *** | 32.5 ± 30.5 *** | 0.0 ± 0.0 |

Remarks:
1) The data is shown mean ± standard deviation (SD).
2) The data of t he self-negative controls of each administration group are consistent (that is, all are 0), so only the data of one self-negative control is presented.
2)  p < 0.01, * p < 0.001, compared with self-negative control, two-factor analysis of variance.

The above examples are only preferred embodiments of the present invention and are not intended to limit the scope of the present invention. The essential technical content of 3. The method of use of the compound of claim 1, wherein $R_1$ represents methyl or ethyl, and $R_2$ represents methyl or ethyl.

4. The method of use of the compound of claim 1, wherein n=1 or 2.

5. The method of use of the compound of claim 1, wherein the compound represented by Formula 1 is selected from the group consisting of the following compounds:

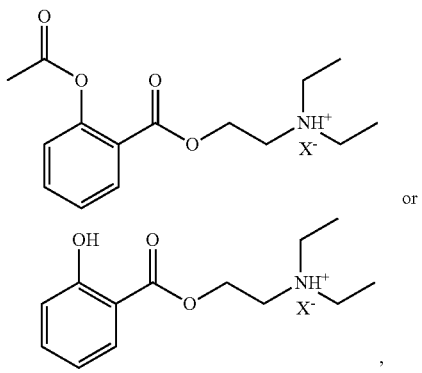

where X⁻ represents an anion.

6. The method of use of the compound of claim 1, wherein the local anesthetic drug comprises at least a separated solid portion and a separated liquid portion, where the solid portion includes a therapeutically effective amount of a compound represented by Formula 1, and the liquid portion includes a pharmaceutically acceptable solvent.

7. The method of use of the compound of claim 6, wherein the pharmaceutically acceptable solvent is selected from the group consisting of sterile water, decarbonated water, ethanol, sorbitol aqueous solution, and physiological saline.

8. The method of use of the compound of claim 6, wherein the solid portion is stored in a hermetic, pharmaceutically acceptable packaging material.

9. The method of use of the compound of claim 6, wherein, when the local anesthetic drug is used, the solid portion is mixed with the liquid portion.

10. The method of use of the compound of claim 2, wherein the monovalent anion is one of Cl⁻, Br⁻, F⁻, I⁻, AcO⁻, oxalate, dihydrogen phosphate, citrate and thiocyanate group.

11. The method of use of the compound of claim 5, wherein the anion is a monovalent anion.

12. The method of use of the compound of claim 11, wherein the monovalent anion is one of Cl⁻, Br⁻, F⁻, I⁻, AcO⁻, oxalate, dihydrogen phosphate, citrate and thiocyanate group.

13. The method of use of the compound of claim 5, wherein the compound represented by Formula 1 is 2-(diethylamino)-ethyl-2-acetoxybenzoate hydrochloride or salicylic acid-(2-diethylaminoethyl ester) hydrochloride.

14. The method of use of the compound of claim 8, wherein the pharmaceutically acceptable packaging material is selected from the group consisting of a low density polyethylene film, a low density polyethylene bag, a high density polyethylene film, a high density polyethylene bottle, a polypropylene bottle, a poly(ethylene terephthalate) bottle, a film of at least one selected from the group consisting of polyester, aluminum, and polyethylene, a composite bag of at least one selected from the group consisting of polyester, aluminum, and polyethylene, a glass bottle, or a combination thereof.

* * * * *